Dec. 24, 1946. F. A. SCHELL Plant Pat. 720
APPLE TREE
Filed Jan. 29, 1946
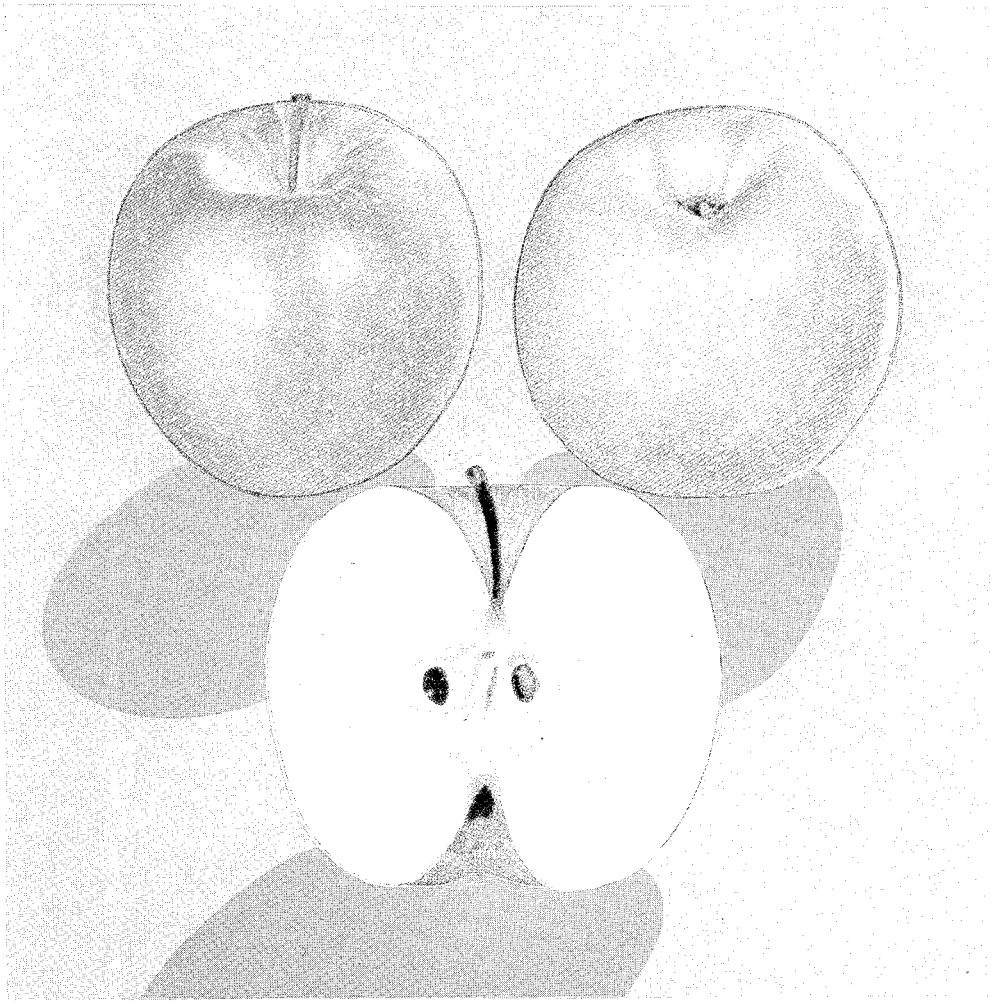
Inventor
F. A. Schell
By Robb & Robb
attorneys Patented Dec. 24, 1946

Plant Pat. 720

UNITED STATES PATENT OFFICE

720

APPLE TREE

Frank A. Schell, Cashmere, Wash., assignor to Stark Bro's Nurseries and Orchards Company, Louisiana, Mo., a corporation of Missouri Application January 29, 1946, Serial No. 644,055

1 Claim. (Cl. 47—62)

This discovery relates to a new and distinct variety of apple tree, originating as a chance seedling.

This new apple is characterized as to novelty by its habits of bearing heavy crops of fruit which are of a deep red color all over and which develop the finest mild flavor several weeks before the well-known "Jonathan" variety attains eating quality and yet keeps well in storage.

The fruit referred to has a flavor similar to that of the "Starking" variety, a shape comparable to that of "Grimes Golden," and an all-over red color resembling that of "Starking." It attains full flavor before either "Jonathan," "Grimes Golden," or "Golden Delicious" are fully matured and, as indicated above, keeps well in storage throughout the "Jonathan" season.

In the accompanying drawing are illustrated obverse perspective views of specimens of the fruit and a sectional view thereof, showing clearly the shape, core and other important characteristics hereinafter more specifically described and claimed.

Asexual reproduction of the new variety discloses that these important characteristics are established or fixed.

The following is a detailed description of this new variety, in which color terminology accords with the general dictionary significance of the terms employed, except where indicated to be in accord with Ridgway's Color Standard:

Tree: Medium size; vigorous; upright; tall; round-topped; rapid growing; hardy; very productive; regular bearer.

*Trunk:* Medium stocky; smooth.

*Branches:* Medium thick; smooth; much branching; grey. *Lenticels*—numerous; large.

*Leaves:* Length, 3½ inches; width, 2½ inches. Medium size; wide; medium long; oval; abruptly pointed; medium thick; medium green; smooth. *Margin*—coarsely serrate. *Petiole*—medium long; medium thick.

Flowers: Dates of first and full bloom—April 7, 1945, and April 10, 1945, at Louisiana, Missouri. Medium early compared with other varieties. Medium size; white.

Fruit: Maturity when described—eating, September 15, 1945.

*Size.*—Uniform. Axial diameter, 2.7 inches; transverse, 2.85 inches. Oblong.

*Cavity.* — Symmetrical; abrupt at base; rounded; acuminate; undulate; pubescent toward apex.

*Basin.*—Symmetrical; abrupt at base; rounded; wide; furrowed; crowned; pubescent. Depth, ¼ inch breadth, 1 inch.

*Stem.*—Medium stout; pubescent. Length, ⅞ to 1⅛ inches; breadth, $\frac{1}{10}$ inch. Markings—Brown with white pubescence.

*Calyx.*—Open; segments persistent; broadly lanceloate. Length, ¼ inch. Separated at base; ascending; reflexed from base at apex; converged from base toward center. Outer surface—pubescent; inner surface—pubescent.

*Eye.*—Large; partially closed.

*Skin.*—Thick; tough; smooth; glossy; waxed. Dots conspicuous; many small; depressed; circular. Color of dots, salmon; distribution of dots, most near basin. Ground color, pale yellow. *Color markings*—self-colored; bright. Color of markings, Oxblood Red (Ridgway). *Bloom*—scant. *Scarfskin*—wanting. *General color effect*—Bright Nopal Red to Carmine (Ridgway).

Flesh: Rather juicy.

*Color of flesh.*—White with yellowish tint, tinged with red in cortex near skin.

*Texture.*—Firm.

*Flavor.*—Mild; rich. Quality—best.

Core: Median.

*Bundle area.*—Medium size; oblate; cordate; symmetrical. Halves of area—unequal.

*Bundles.*—Green-yellowish, reddish tinge; conspicuous; two whorls. Alternate bundle—reaches tube above stamens.

*Core lines.*—Clasping. In cross section—distinct.

*Carpellary area.*—Indistinct; large.

*Calyx tube.*—Pubescent toward base; apex broadly funnel form. Stem of funnel—medium long. Depth of tube to shoulder—⅕ inch; entire depth, ½ inch.

*Styles.*—Present; united toward base; pubescent throughout.

*Stamens.*—One distinct whorl; basal.

*Axillary cavity.*—Present.

*Seed cells.*—Abaxile; closed. Cell walls—distant; thin; tough. Length, $\frac{6}{10}$ inch; breadth, $\frac{4}{10}$ inch. Longitudinal section—broadly cordate. Surface—fissured; tufted.

Seeds:

*Number perfect.*—8 to 10. *Imperfect*—1 to 2. *Largest*—10.

*Number in one cell.*—2. Length, ⅓ inch; breadth, $\frac{2}{16}$ inch. Form—obtuse.

*Color.*—Brown.

Use: Dessert.

Keeping quality: Good.

I claim:

A new and distinct variety of apple tree characterized as to novelty by the habit of bearing heavy crops of fruit having a shape resembling that of "Grimes Golden," a flavor comparable to that of "Starking," a deep brilliant red color all over; by the attainment of a fine, full, mild flavor before "Grimes Golden" or "Jonathan," grown under comparable conditions, reach the best eating stage, and by the good keeping quality of the fruit in storage, substantially as shown and described.

FRANK A. SCHELL.